United States Patent [19]
Turner

[11] Patent Number: 5,133,759
[45] Date of Patent: Jul. 28, 1992

[54] ASYMMETRICAL FEMORAL CONDYE TOTAL KNEE ARTHROPLASTY PROSTHESIS

[76] Inventor: Richard H. Turner, 4999 Heyden Run Rd., Columbus, Ohio 43221

[21] Appl. No.: 705,404

[22] Filed: May 24, 1991

[51] Int. Cl.$^5$ .............................................. A61F 2/38
[52] U.S. Cl. ....................................... 623/20; 623/18
[58] Field of Search .......................... 623/20, 18, 16

[56] References Cited

U.S. PATENT DOCUMENTS

| | | | |
|---|---|---|---|
| 3,774,244 | 11/1973 | Walker | 3/1 |
| 3,868,730 | 3/1975 | Kaufer et al. | 3/1 |
| 3,869,731 | 3/1975 | Waugh et al. | 3/1 |
| 3,918,102 | 11/1975 | Eichler | 3/1.912 |
| 4,034,418 | 7/1977 | Jackson et al. | 3/1.911 |
| 4,094,017 | 6/1978 | Matthews et al. | 3/1.911 |
| 4,207,627 | 6/1980 | Cloutier | 623/20 |
| 4,224,696 | 9/1980 | Murray et al. | 3/1.911 |
| 4,224,697 | 9/1980 | Murray et al. | 3/1.911 |
| 4,257,411 | 3/1981 | Cho | 128/92 EB |
| 4,298,992 | 11/1981 | Burstein et al. | 3/1.911 |
| 4,344,193 | 8/1982 | Kenny | 3/1.911 |
| 4,348,859 | 11/1982 | Schurman et al. | 3/1.911 |
| 4,501,266 | 2/1985 | McDaniel | 128/69 |
| 4,524,766 | 6/1985 | Petersen | 128/92 |
| 4,586,933 | 5/1986 | Shoji et al. | 623/20 |
| 4,630,601 | 12/1986 | Harder et al. | 128/92 YZ |
| 4,662,889 | 5/1987 | Zichner et al. | 623/20 |
| 4,712,541 | 12/1987 | Harder et al. | 128/92 YY |
| 4,723,539 | 2/1988 | Townsend | 128/80 C |
| 4,769,040 | 9/1988 | Wevers | 623/20 |
| 4,773,404 | 9/1988 | Townsend | 128/80 C |
| 4,773,417 | 9/1988 | Moore et al. | 128/303 R |
| 4,779,349 | 10/1988 | Odensten et al. | 33/143 R |
| 4,881,537 | 11/1989 | Henning | 606/84 |
| 4,888,020 | 12/1989 | Horber | 623/20 |
| 4,915,092 | 4/1990 | Firica et al. | 606/67 |
| 4,928,670 | 5/1990 | DeLorenzo | 128/80 C |
| 4,935,023 | 6/1990 | Whiteside et al. | 606/88 |
| 4,950,298 | 8/1990 | Gustilo et al. | 623/20 |
| 4,963,152 | 10/1990 | Hofmann et al. | 623/18 |

FOREIGN PATENT DOCUMENTS

| 2288509 | 5/1976 | France | 623/20 |

OTHER PUBLICATIONS

Journal of Orthopaedic Research, published, 1986, *The Three-Dimensional Tracking Pattern of the Human Patella*, van Kampen, A., and Huiskes, R.

The Journal of Bone and Joint Surgery, Incorporated, published 1989, *The Effect of Alignment of the Implant on Fractures of the Patella after Condylar Total Knee Arthroplasty*, Figgie et al.

Automedica, published 1989, *Computer-Aided Knee Prosthesis Design and Analysis*, Hoeltzel et al.

Biomechanical Research Laboratory, *The Effect of Axial Rotation of the Femoral Component on Knee Stability and Patellar Tracking in Total Knee Arthroplasty*.

*Primary Examiner*—Ronald Frinks
*Attorney, Agent, or Firm*—John L. Gray

[57] ABSTRACT

A total knee arthroplasty prosthesis wherein the lateral femoral condyle is recessed more into the femur and is sloped cephalod and posterior when implanted on the femur when compared with the medial femoral condyle.

5 Claims, 3 Drawing Sheets

ASYMMETRICAL FEMORAL CONDYE TOTAL KNEE ARTHROPLASTY PROSTHESIS

BACKGROUND OF THE INVENTION

Total replacement of the anatomical knee joint with a prosthetic joint has become an accepted, increasingly commonplace, surgical procedure. At the present time the femoral prosthesis is provided with symmetrical medial and lateral condyles. The disadvantage of the use of this type of prosthesis in total knee arthroplasty surgery results in excessive compression force on the patellar component at the patella lateral femoral condyle articulation producing patellar component failure with unacceptable frequency and decreased range of motion due to the tightness of the patella as it moves over the condyle during flexion and extension of the knee.

The shape of the prosthesis is one of the most important factors influencing post-operative knee function and the duration of prosthesis survival.

SUMMARY OF THE INVENTION

The present invention designates a femoral prosthesis where the lateral femoral condyle, that which is nearest the outer side of the knee, is displaced vertically above the medical femore condyle so as to be recessed more into the femur than is the medial femoral condyle. In addition, the lateral femoral condyle is sloped cephalad and posterior when implanted on the femur compared with the inner or medial femoral condyle. Preferably this sloped portion is located in the mid portion of the lateral femoral condyle. Moreover, since the lateral femoral condyle is also slightly recessed toward the femur as compared with the medial femoral condyle, as the knee is bent, the patella initially moves in the patellar groove and then is permitted to shift toward the lateral femoral condyle and thus more readily approach its natural movement, thus diminishing patello femoral compression forces.

It is therefore an object of this invention to provide an asymmetrical femoral condyle total knee arthroplasty prosthesis wherein the lateral femoral condyle is slightly recessed toward the femur as compared with the medial femoral condyle.

It is also an object of this invention to provide such a prosthesis wherein the lateral femoral condyle is sloped cephalad and posterior when implanted on the femur, preferably over its mid portion, as compared with the medial femoral condyle.

It is a still further object of this invention to provide such a prosthesis which permits the patella to assume a more normal route of travel as the knee is flexed or extended.

These, together with other objects and advantages of the invention will become more readily apparent to those skilled in the art when the following general statements and descriptions are read in the light of the appended drawings.

DETAILED DESCRIPTION OF THE INVENTION

Figure 1:
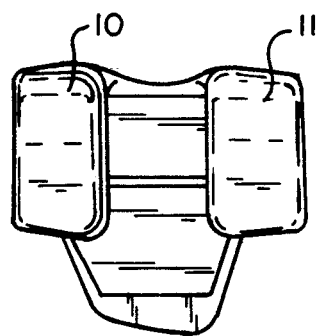
FIGS. 1 and 2 show, respectively, a front view and a side elevation view of the prior art devices.
Figure 2:
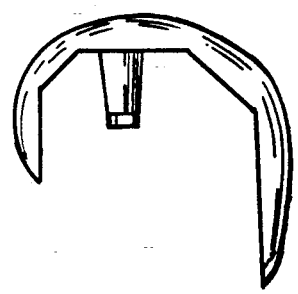
Figure 3:
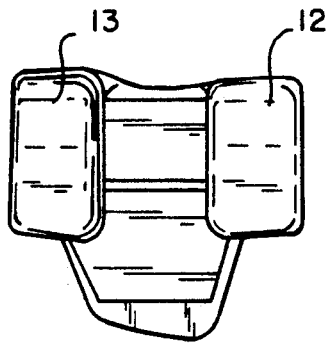
FIGS. 3 and 4 show the same views of the present invention.
Figure 4:
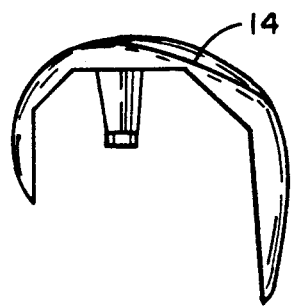
Figure 5:
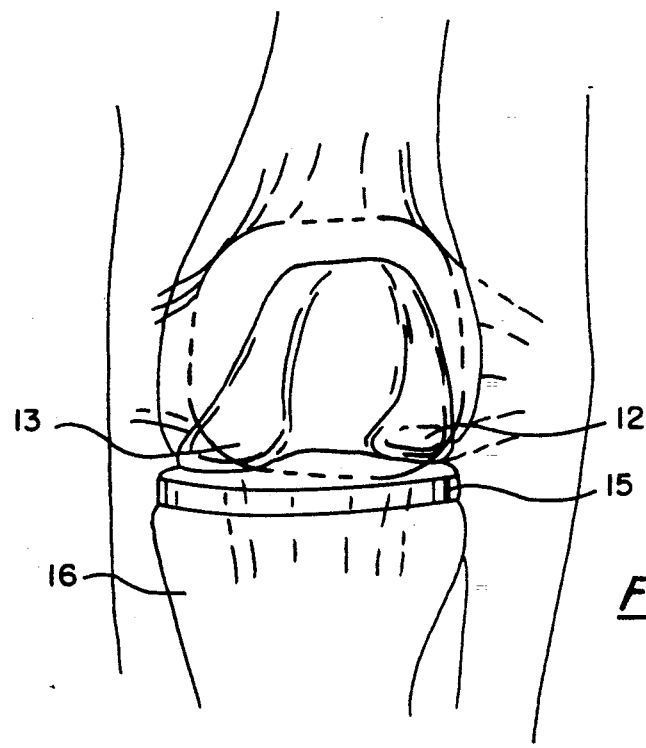
FIG. 5 shows the present invention positioned in the knee joint.

FIGS. 1 and 2 show the prior art devices wherein it will be noted that condyles 10 and 11 as shown in FIG. 1 are at the same elevation and have the identical continuous curvature as shown in FIG. 2. Referring now more particularly to FIG. 3, the invention is shown with the lateral femoral condyle 12 being connected to and displaced vertically above the medial femoral condyle so as to be recessed more into the femur than is the medial femoral condyle 13. Not only is the lateral femoral condyle 12 recessed more into the femur than is the medial femoral condyle 13, but it is also somewhat sloped as shown at 14 in FIG. 4. The invention is shown in FIG. 5 positioned on the insert 15 at the upper end of the tibia 16.

Figure 6:
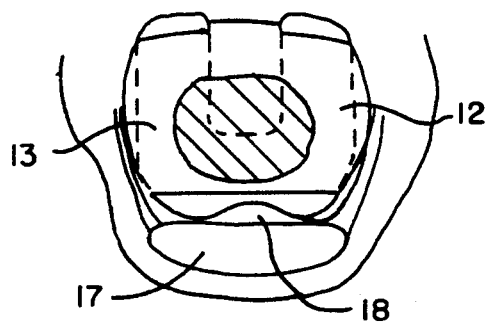
FIG. 6 is a section 6—6 of FIG. 7 showing the prosthesis of the present invention installed in the femur and positioned with respect to the patella with the leg in a vertical position.
Figure 7:
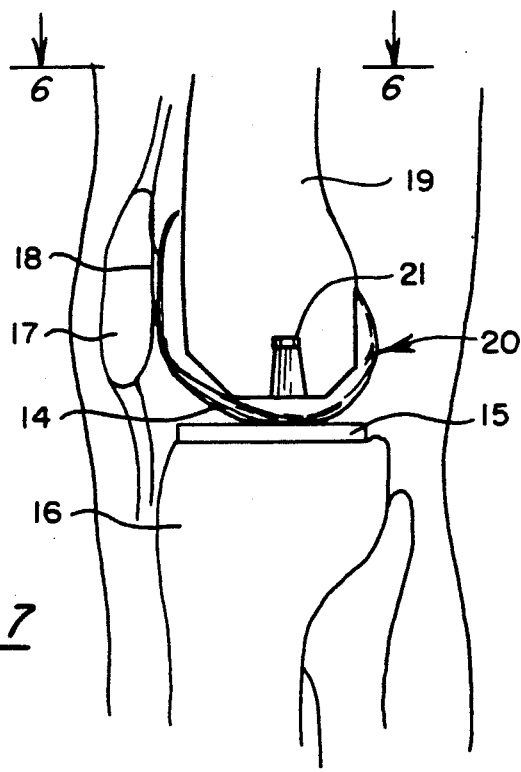
FIG. 7 is a side view of the prosthesis of the present invention installed in the femur with the leg in the vertical position.

Referring now more particularly to FIG. 6, which is a section of FIG. 7 on section 6—6, the patella is shown at 17 with the lateral femoral condyle 12 and the medial femoral condyle 13 also shown. When necessary, a plastic patellar component 18 is attached to the inner side of the patella 17 which articulates with the condyles 12 and 13 as the knee is flexed or extended.

Turning now more particularly to FIG. 7 the femur 19 is shown with the prosthesis identified generally at 20 installed on the femur. Also shown are the femoral component lugs 21—21. The tibia 16 has an upper plastic insert 15 and the sloped portion 14 of the lateral femoral condyle 12 is also shown in relative position to the patella 17 and the patellar component guide 18.

Figure 8:
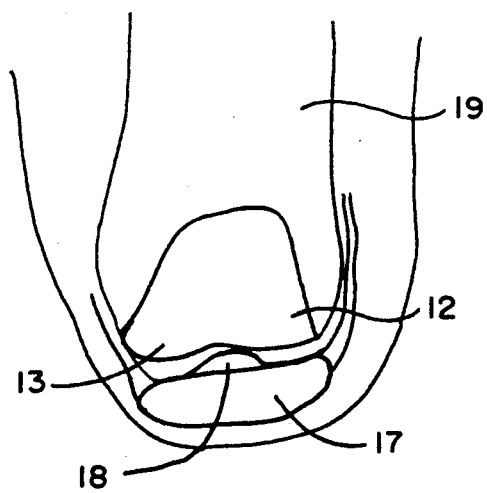
FIG. 8 is a vertical view of the present invention and its relationship to the patella as the leg is bent at an approximate 60° angle as shown in the side elevation view of FIG. 9.
Figure 9:
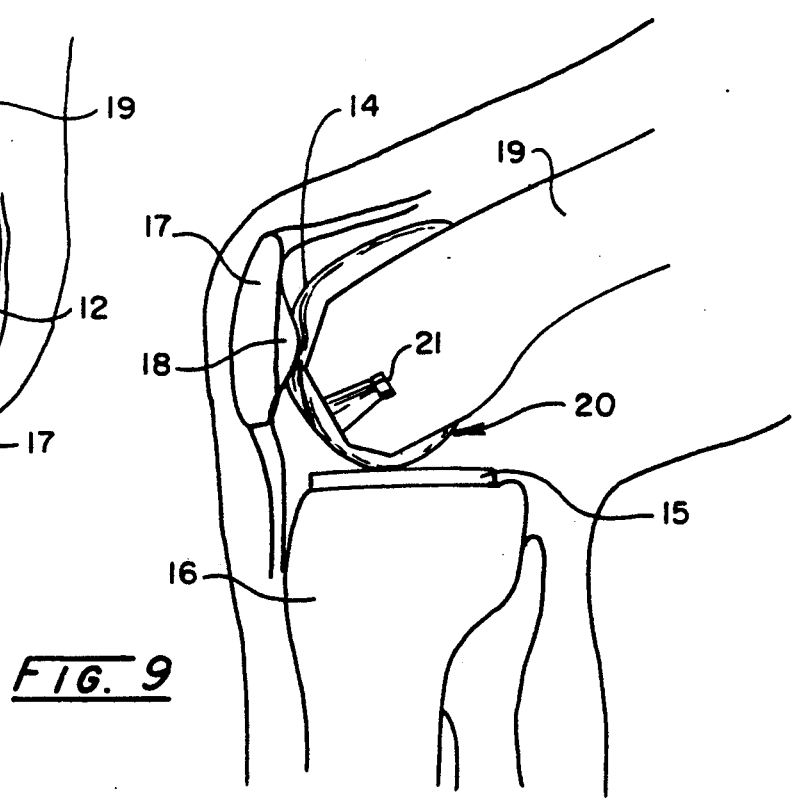

Referring now more particularly to FIGS. 8 and 9, the knee is shown positioned at approximately 60 degrees of flexion. In FIG. 8 it will be seen that the patella 17 and the plastic patellar component 18 have moved laterally to some extent over the lateral femoral condyle 12 portion of the prosthesis so as to minimize the patellar femoral force with quadriceps use while flexing or extending the knee.

Referring now to FIG. 9, it will be seen that the plastic patellar component 18 associated with the patella 17 engages the sloped portion 14 of the lateral femoral condyle 12, thus further minimizing the patellar femoral compression force.

Figure 10:
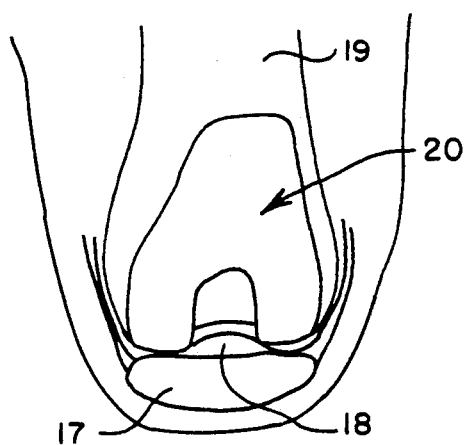
FIG. 10 is a vertical view of the present invention in relationship to the patella as the leg is further bent to an approximate 100° angle as shown in the side elevation view of FIG. 11.
Figure 11:
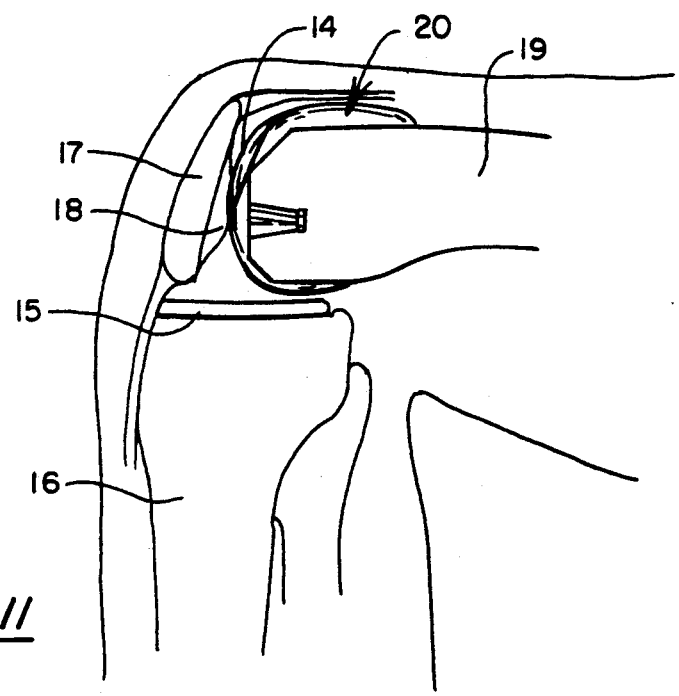

Referring now to FIGS. 10 and 11, the knee is shown flexed at an approximate 100 degree angle. It will be seen that the patella 17 has now reached the central open portion between the two condyles 12 and 13 having traversed the lateral femoral condyle 12 and the sloped portion 14 of the lateral femoral condyle 12. The use of this prosthesis permits the patella 17 more nearly to mimic the normal movement in its travel as the knee is bent or extended.

While this invention has been described in its preferred embodiment, it is to be appreciated that variations therefrom may be made without departing from the true scope and spirit of the invention.

What is claimed is:

1. An asymmetrical femoral condyle knee arthroplasty prosthesis comprising a lateral femoral condyle and a connected medial femoral condyle, said lateral femoral condyle being displaced vertically above said medial femoral condyle whereby said lateral femoral condyle is adapted to be recessed further into the femur than is said medial femoral condyle when implanted in the femur.

2. The prosthesis of claim 1 wherein said lateral femoral condyle is also sloped cephalad and posterior when implanted on the femur as compared with said medial femoral condyle.

3. The prosthesis of claim 2 wherein said sloped cephalad and posterior portion of said lateral femoral condyle is in the mid portion of said lateral femoral condyle.

4. The prosthesis of claim 1 wherein the difference between the amount that said lateral femoral condyle is adapted to be recessed further into the femur when compared with the amount that said medial femoral condyle is adapted to be recessed into the femur is sufficient to permit the patella to minimize patellar femoral force when flexing or extending the knee.

5. The prosthesis of claim 2 wherein the amount that said lateral femoral condyle is sloped cephalad and posterior when implanted on the femur as compared with said medial patellar femoral force when flexing or extending the knee.

* * * * *

UNITED STATES PATENT AND TRADEMARK OFFICE
CERTIFICATE OF CORRECTION

PATENT NO. : 5,133,759
DATED : July 28, 1992
INVENTOR(S) : Richard H. Turner

It is certified that error appears in the above-indentified patent and that said Letters Patent is hereby corrected as shown below:

On the title page, Item [54] and Col. 1, line 1, the letter "L" was omitted in the word "CONCYLE".

Column 4, line 15, after the word "medial" insert "femoral condyle, is sufficient ot permit the patella to minimize".

Signed and Sealed this

Twenty-fourth Day of August, 1993

Attest:

BRUCE LEHMAN

*Attesting Officer*  *Commissioner of Patents and Trademarks*